(12) United States Patent
Stergiopulos

(10) Patent No.: US 9,375,347 B2
(45) Date of Patent: Jun. 28, 2016

(54) NON-INVASIVELY ADJUSTABLE DRAINAGE DEVICE

(75) Inventor: Nikolaos Stergiopulos, Preverenges (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 0 days.

(21) Appl. No.: 12/743,955

(22) PCT Filed: Nov. 23, 2007

(86) PCT No.: PCT/IB2007/054771
§ 371 (c)(1),
(2), (4) Date: Oct. 18, 2010

(87) PCT Pub. No.: WO2009/066133
PCT Pub. Date: May 28, 2009

(65) Prior Publication Data
US 2011/0066098 A1    Mar. 17, 2011

(51) Int. Cl.
*A61M 5/00*    (2006.01)
*A61F 9/007*   (2006.01)
*A61M 27/00*   (2006.01)
*F16K 3/34*    (2006.01)

(52) U.S. Cl.
CPC .......... *A61F 9/00781* (2013.01); *A61M 27/002* (2013.01); *A61M 27/006* (2013.01); *A61M 2205/3515* (2013.01); *F16K 3/34* (2013.01)

(58) Field of Classification Search
CPC ............ A61F 9/00781; A61M 27/002; A61M 27/006; A61M 16/20; A61M 27/00; A61M 2027/004; A61M 2205/3515; A61M 2205/3523; F16K 3/34; F16K 7/00

USPC .................................................. 604/9; 623/24
See application file for complete search history.

(56) References Cited

U.S. PATENT DOCUMENTS

| | | | | |
|---|---|---|---|---|
| 3,926,175 A | * | 12/1975 | Allen et al. | 600/30 |
| 4,140,011 A | * | 2/1979  | Krupa et al. | 73/170.17 |
| 4,156,422 A | * | 5/1979  | Hildebrandt | A61M 27/006 600/561 |
| 4,457,757 A | | 7/1984 | Molteno | |
| 4,515,588 A | * | 5/1985 | Amendolia | 604/118 |
| 5,300,020 A | | 4/1994 | L'Esperance | |
| 5,308,040 A | * | 5/1994 | Torres | 251/208 |
| 5,342,025 A | | 8/1994 | Hwang | |
| 5,411,473 A | | 5/1995 | Ahmed | |
| 5,626,558 A | | 5/1997 | Suson | |

(Continued)

FOREIGN PATENT DOCUMENTS

| | | | |
|---|---|---|---|
| EP | 1243826 A | | 9/2002 |
| EP | 1243826 A2 | * | 9/2002 |

(Continued)

OTHER PUBLICATIONS

Official Action with English translation for Japan Patent Application No. 2010-534553, mailed Sep. 11, 2012, 5 pages.

(Continued)

*Primary Examiner* — Tatyana Zalukaeva
*Assistant Examiner* — Ariana Zimbouski
(74) *Attorney, Agent, or Firm* — Sheridan Ross P.C.

(57) ABSTRACT

The device comprises at least an inlet tube for the passage of fluid to be drained, said tube being connected to a chamber wherein said chamber comprises rotating means for adjusting the flow rate in said tube.

3 Claims, 5 Drawing Sheets

(56) References Cited

U.S. PATENT DOCUMENTS

| | | | |
|---|---|---|---|
| 6,050,969 A * | 4/2000 | Kraus | 604/9 |
| 6,077,299 A * | 6/2000 | Adelberg et al. | 623/24 |
| 6,168,575 B1 | 1/2001 | Soltanpour | |
| 6,186,974 B1 | 2/2001 | Allan et al. | |
| 6,508,779 B1 | 1/2003 | Suson | |
| 6,589,198 B1 | 7/2003 | Soltanpour et al. | |
| 6,726,664 B2 | 4/2004 | Yaron et al. | |
| 2001/0022350 A1 | 9/2001 | Ito | |
| 2005/0085763 A1* | 4/2005 | Ginggen et al. | 604/9 |
| 2007/0005000 A1* | 1/2007 | Ludin | 604/9 |
| 2008/0228127 A1* | 9/2008 | Burns et al. | 604/9 |
| 2009/0182263 A1* | 7/2009 | Burbank et al. | 604/28 |
| 2010/0152524 A1* | 6/2010 | Sentmanat | 600/16 |

FOREIGN PATENT DOCUMENTS

| | | |
|---|---|---|
| JP | 2001-170162 | 6/2001 |
| JP | 2006-034506 | 2/2006 |
| JP | 2009-535102 | 11/2007 |
| WO | WO 99/62586 A | 12/1999 |
| WO | WO 99/66862 A | 12/1999 |
| WO | WO 9962586 A1 * | 12/1999 |
| WO | WO 2007/127305 | 11/2007 |

OTHER PUBLICATIONS

International Search Report prepared by the European Patent Office on Jul. 2, 2008, for International Application No. PCT/IB2007/054771.

Written Opinion prepared by the European Patent Office on Jul. 2, 2008, for International Application No. PCT/IB2007/054771.

* cited by examiner

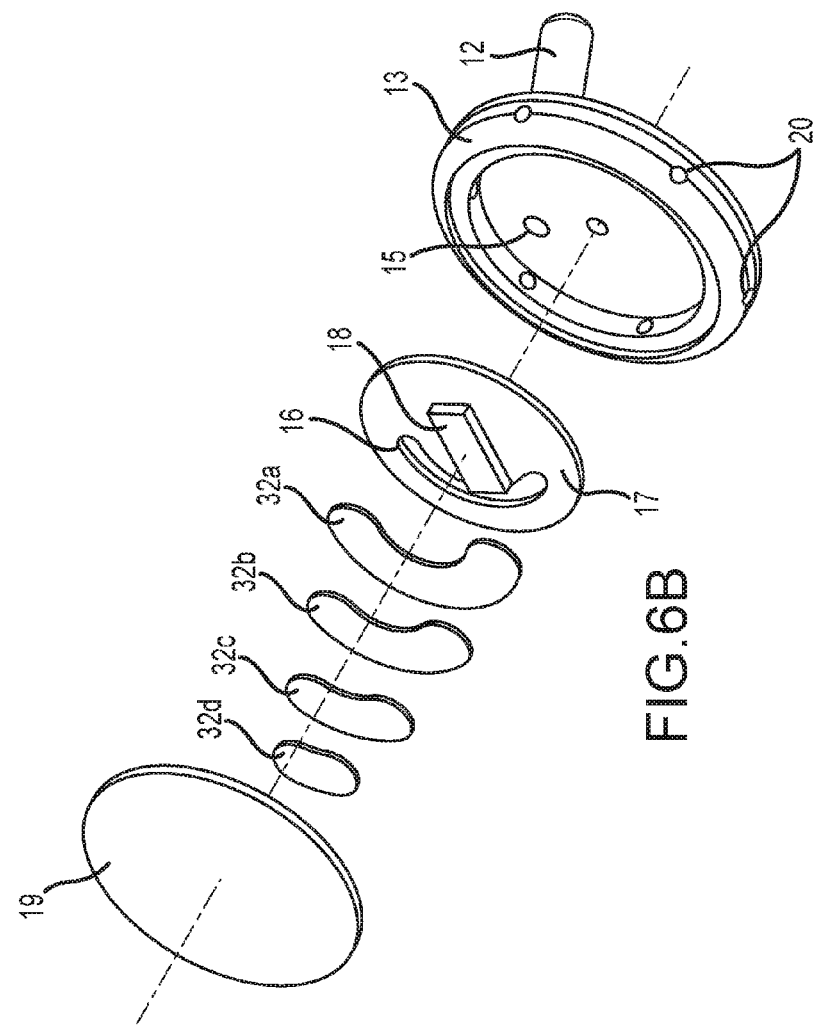
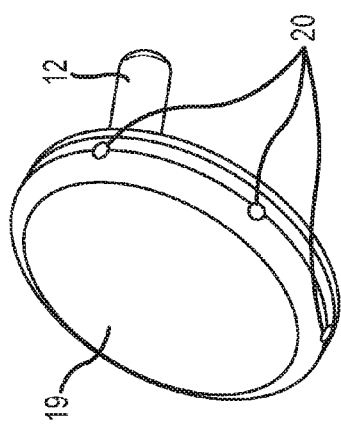
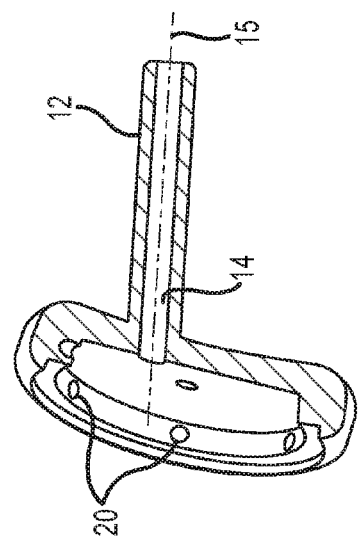

NON-INVASIVELY ADJUSTABLE DRAINAGE DEVICE

CROSS REFERENCE TO RELATED APPLICATIONS

This application is a national stage application under 35 U.S.C. 371 of PCT Application No. PCT/IB2007/054771 having an international filing date of 23 Nov. 2007, which designated the United States, the entire disclosure of which is incorporated herein by reference.

TECHNICAL FIELD

The present invention concerns an implantable adjustable drainage device for draining body fluids. More specifically, the present invention concerns a non-invasively adjustable drainage device used for example for the treatment of glaucoma.

BACKGROUND ART

Implantable adjustable drainage devices are known in the art, especially in the field of treatment of glaucoma.

Glaucoma is a disorder associated with high pressure in the eye, and is characterized by damage to the optic nerve, with consequent visual loss, initially peripheral, but potentially blinding if relentlessly progressive. Unfortunately, glaucoma is usually a disease in which the patient is entirely asymptomatic (without symptoms) until late in the disease. Glaucoma affects about 70 millions of people worldwide.

While traditional treatment of glaucoma is through medication for example eye drops lowering the production of intraocular fluid (aqueous humor), in certain cases this treatment fails and other surgical treatments are preferred, such as filter procedures or placement of a glaucoma drainage device ("GDD") with a drainage tube. GDDs help evacuate intraocular fluid by providing an artificial drainage pathway, thus maintaining a low intraocular pressure ("IOP").

Typically, the GDD is inserted through a small incision made in the conjunctiva. The surgeon then makes a tiny incision in the sclera of the eye and fashions an opening for the drainage implant device. The drainage tube is placed such that the opening of the tiny tube is inside the anterior chamber of the eye where it is bathed in aqueous fluid. The tube is sutured in place with the drainage device attached to the sclera of the eye. Most surgeons will place an absorbable suture around the tube at the time of surgery to prevent filtration through the device until a fibrous capsule has formed. As such, the device is not expected to function until about 3 to 8 weeks following the procedure. This technique is thought to prevent over-filtration.

A glaucoma passive drainage device of the prior art is described in U.S. Pat. No. 4,457,757 to Molteno. The Molteno device comprises in particular a tube made of a biologically inert silicone tubing for insertion into the eye in order to drain the aqueous humor from the anterior chamber of the eye. This device does not have a pressure regulating mechanism and only relies on the pressure regulation provided by the resistance to aqueous flow of the tubing.

One of the major problems of such device is that it is totally passive, i.e., the drainage flow depends on IOP and on the fixed hydrodynamic resistance of the shunt. In many cases, however, the hydrodynamic resistance of the shunt may not be optimal which may lead to high IOP, when the resistance is high, or to over-drainage, if the resistance is low.

This problem has been recognised in the prior art and several publications relate to improvements of the known device such that the flow can be controlled and adapted.

Another example is illustrated in U.S. Pat. No. 5,411,473 to Ahmed. In this patent, the idea is to add a system to a drainage device, in which the system has a membrane folded and held in tension between two plates to provide a slit opening. The membrane responds to pressure changes to open or close the slit opening. All the characteristics of the system are based on the properties of the membrane itself and this element cannot be changed easily.

Another example is illustrated in U.S. Pat. No. 5,300,020 to L'Esperance where the drainage system comprises flow control means. In this patent, said means are in the form of a plug of absorbable material having porous properties which maintains anterior chamber pressure. Once the aqueous fluid has been totally absorbed into the plug, a path of relatively slow drainage flow will be established into the subconjunctival space until an equilibrium of pressures is developed. The pressure release is slow enough to avoid a collapse of the cornea yet sufficient to lower the intraocular pressure.

As one will readily understand, a disadvantage of this solution is that it has certain inertia and the flow rate may not be changed to adapt to the circumstances.

In another embodiment disclosed in this patent, the system comprises a flexible drainage tube with a time-delay valve-opening structure. This structure comprises a ball of biocompatible absorbable material as means of applying a valve-closing squeeze on the tube. As the body fluid gradually dissolve the material of the ball, the valve-closing force of the ball is reduced to create a valve opening condition. In a further embodiment, the valve-opening structure comprises polymer components which either inherently or by reason of special compounding are selectively shrinkable or stretchable to effect opening and/or closure operation of the valve device.

In this embodiment, it is clear that a precise adjustment of the flow rate of the drainage is difficult to realize over time and once the ball has dissolved, it is not possible to regulate the flow anymore.

Other examples are disclosed in the following prior art publications U.S. Pat. No. 5,626,558, U.S. Pat. No. 6,186,974, U.S. Pat. No. 6,508,779 or U.S. Pat. No. 6,726,664.

U.S. Pat. No. 6,077,299 to Adelberg et al. discloses a non-invasively adjustable valve implant for the drainage of aqueous humor in glaucoma. An aim of the device disclosed in this patent is to provide an implant with a flow characteristic that can be adjusted in a non-invasive manner. More specifically, this device comprises an implant with an inlet tube that is surgically inserted in the anterior chamber of the eye allowing aqueous humor to flow from the anterior chamber to a valve. After passing through the pressure and/or flow regulating valve in the implant, the fluid is dispersed along the periphery of the implant to the interior of the Tenon's capsule where it is absorbed by the body. In one embodiment, the valve inhibits flow below and allows flow above a specific pressure difference between the intraocular pressure within the eye and the pressure within the bleb cavity in Tenon's capsule. The specified pressure difference or set-point is always positive and the valve is always closed for negative pressure differences to prevent reverse flow of fluid from the Tenon's capsule back into the anterior chamber of the eye.

In this patent, the valve is formed by a chamber to which the inlet tube is connected, said chamber being closed by pressure sensitive valve made of a flexible material, such as silicone, in the shape of a flat cone. The pressure regulation set point of the valve is governed by a flexible diaphragm cooperating with an armature plate having an inclined surface configured to slide over a complementary inclined surface that is attached to the diaphragm. The cooperation of the inclined surface of the plate and the complementary surface causes the diaphragm to deflect depending on where the armature plate is located. The armature plate itself is rotated to carry out this regulation through a rotor and a set of speed-reducing and torque-enhancing gears.

As one will readily understand, the characteristics of the valve depend strongly on one element that is the cone shaped valve. In addition, the regulating mechanism comprises many rotating parts and gears rendering it rather complicated to fabricate. In addition, because of the high number of moving parts, there is also a risk of malfunction of the device.

U.S. Pat. No. 6,168,575 and U.S. Pat. No. 6,589,198 to Soltanpour et al. disclose micro-pump assemblies that can be implanted in the eye for controllably removing excess fluid from the eye in order to treat glaucoma. In these patents, the implanted pumps have a variable pumping rate that can be adjusted either manually or automatically, controlled by the measured intra-ocular pressure. The disadvantage of such device is in particular the fact that they are complicated and expensive. Indeed, the device must contain all the necessary elements, in particular electronics and power source and since the device is implanted, these elements must be small and contained in a sealed enclosure. The risk of malfunction is also increased because of the high number of different elements present that must cooperate together.

SUMMARY OF THE INVENTION

Accordingly, an aim of the present invention is to improve the known devices and system.

Another aim of the present invention is to provide a GDD device that is simple to operate, using a reduced number of parts.

A further aim of the present invention is to provide a GDD device that is easy and cheap to fabricate.

BRIEF DESCRIPTION OF THE DRAWINGS

The present invention will be better understood from the description of several embodiments and from the following drawings in which:

FIG. 6 illustrates a fifth embodiment of the invention.

DETAILED DESCRIPTION

In the following description reference will be mainly made to a device that can be used as a GDD (glaucoma drainage device). However, this should not be construed as limiting and other drainage applications may be envisaged for the device according to the invention.

Figure 1:
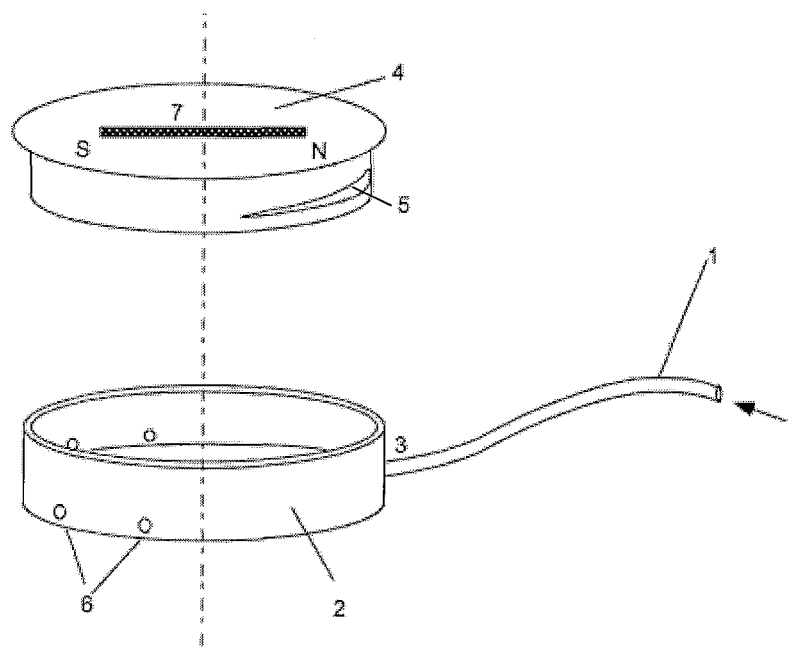
FIG. 1 illustrates a first embodiment of the invention.

In FIG. 1 a schematic diagram of first embodiment of the device is represented. According to the invention, the principle is to adjust the hydrodynamic resistance of the device by means of a rotating disk, which encompasses a variable-section for the passage of fluid. As the disk rotates, clockwise or counterclockwise, the section increases or decreases and the resistance decreases or increases, respectively. To this effect, the device comprises an inlet tube 1, which drains the fluid from the eye (or any other part to be drained) into a hollow shallow container 2. The container is closed hermetically with a gasket 4, which comprises a variable section slit 5 through which fluid can flow from the exit of the tube 3 into the container and thereafter into the outer space through exit holes 6. The gasket 4, although hermetically sealing the container, can rotate around its axis, which is also the axis of rotational symmetry of the container. According to the invention, the rotation of the gasket 4 changes the relative position of the slit 5 with respect to the tube exit 3, thereby imposing a variable resistance to fluid flow. When the gasket is rotated counterclockwise (viewed from the top), the slit section in front of the tube exit 3 decreases, thereby increasing flow resistance, whereas when the rotation is clockwise the slit section increases and resistance to fluid flow decreases.

As one can readily understand, the principle of the system is far simpler than the known device cited above.

It is also necessary to provide means for actuating the rotation of the gasket preferably non-invasively. In order to have a tele-controllable system, one uses, in one embodiment, an applied directional external magnetic field. The proposed procedure and means for achieving this effect are the following: the gasket comprises a permanent magnet 7 that creates a magnetic field, which can easily be detected by placing an external device (i.e. a sensing device) on top of the patient's eye. The sensing device contains a number of sensors, such as magnetoresistive sensors or other equivalent devices, which can sense the magnetic field. The information from the sensors can be combined with the magnetic field equations to derive the amplitude and direction of the magnetic field. This allows the precise determination of the direction of the magnet 7 and, by way of consequence, the rotational position of the gasket 4.

Once the direction of the magnet 7 is known, the user can impose a given rotation to the gasket by applying a strong external magnetic field, which is oriented at a given angle with respect to the actual angle of the magnet 7.

Figure 2:
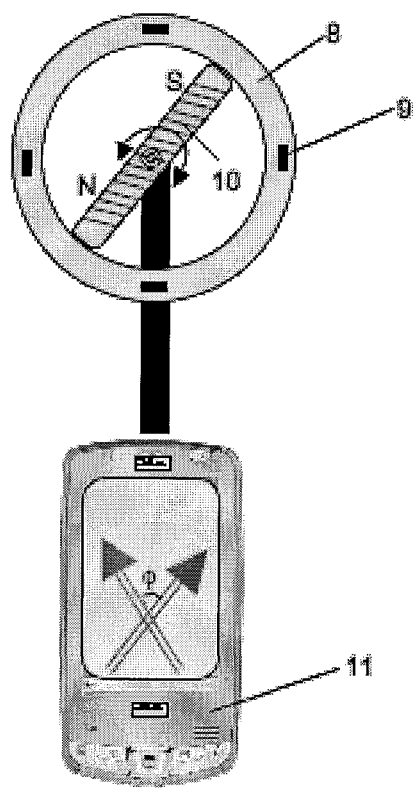
FIG. 2 illustrates an example of an external control device.

This is illustrated schematically in FIG. 2. The strong magnetic field will impose a torque on the magnet, which is proportional to the amplitude of the magnetic field times the magnetic moment of the magnet 7. The torque will force the magnet 7 to align with the imposed magnetic field, thereby imposing a rotation of the gasket equal to the difference in the angles between the original magnet direction and the direction of the imposed magnetic field. With this method, an operator can impose precise and measurable rotations to the gasket, thus obtaining the desired changes in fluidic resistance in the draining device.

Magnetoresistive sensors 9 are placed on a rim 8, which is positioned on top of the patient's eye. The sensors are used to capture and compute the direction of the underlying magnet 7, which is displayed as the vector oriented to the left on the control unit 11 screen. If the user wishes to rotate the gasket 4 by an angle φ clockwise, he/she turns the electromagnet 10 such that its direction illustrated by the vector oriented to the right on the control unit 11 screen forms the desired angle φ with the magnet angle. The user then powers the electromagnet 10, which applies a strong magnetic field with a polarity opposite to that of the magnet and in the direction of the vector oriented to the right. The induced magnetic field applies a strong torque on the underlying magnet 7, which forces the magnet 7 to align with the vector oriented to the right, thus achieving the desired gasket rotation.

In another equivalent design, the rotational electromagnet 10 can be replaced by two fixed orthogonal electromagnets. Upon activation, each of the two orthogonal electromagnets will deliver a magnetic field oriented along its axis. The total magnetic field will be the vector sum of the two individual fields. By choosing the relative intensity of the current fed into each of the electromagnets one can deliver a magnetic field of any desired magnitude and orientation.

Fluidic resistance can be measured for the different rotational positions of the gasket, thereby providing some a priori guidance to the user for selecting the amplitude of rotation needed for obtaining a desired effect on the drainage and the resulting IOP. Otherwise, the user may apply incremental rotations and measure every time the IOP for verifying the optimal position of the gasket 4.

Figure 3:
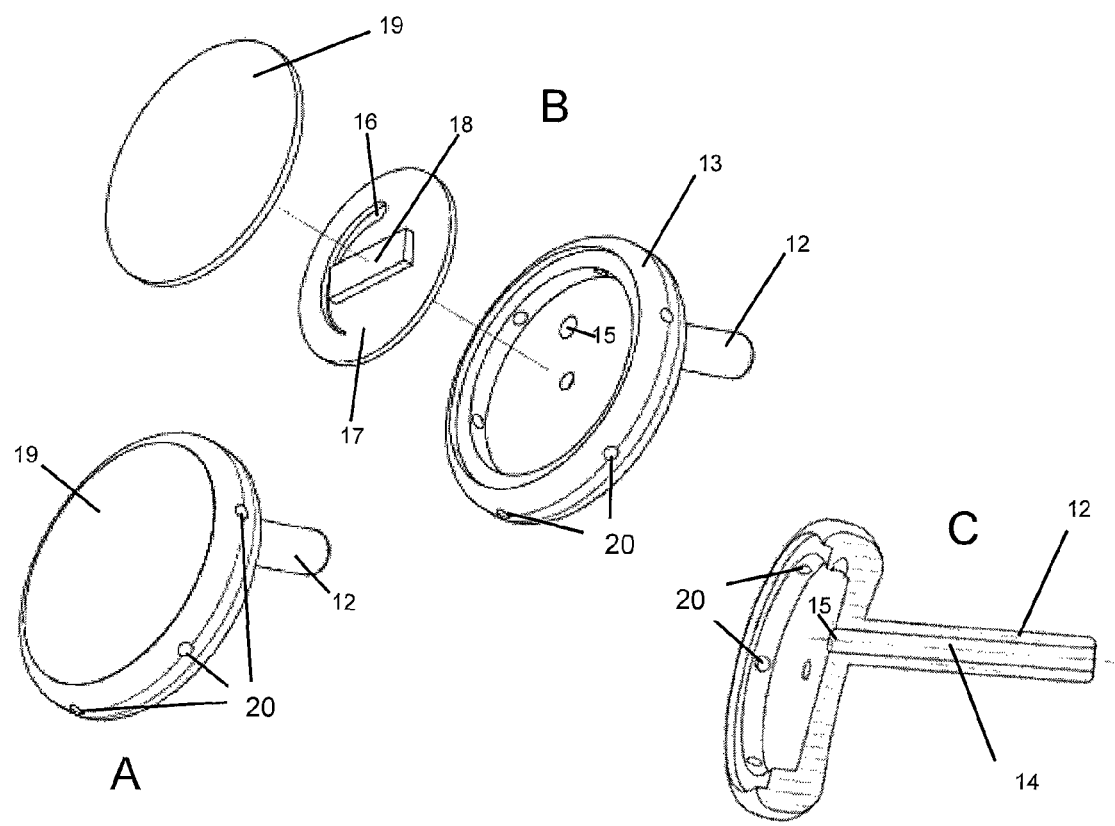
FIG. 3 illustrates a second embodiment of the invention.

Another embodiment of the invention is illustrated in FIG. 3. In this embodiment the tube 12 which is inserted into the intraocular space and acts as fluid conduit is connected to a container 13 either at an normal angle or, in general, at an oblique angle as shown in FIG. 3. The base of the container 13 in contact with the eye is either flat or has a slight spherical curvature, with a radius of curvature of typically 11 mm or similar, which corresponds to the natural radius of curvature of the eye. This curvature is seen in FIG. 3C.

In FIG. 3, "A" shows an assembled view of this embodiment of the invention.

"B" an exploded view of the device where the internal plate 17 containing the variable section slit 16 and the magnet 18 is seen.

"C" A section view of the tube-container assembly with a longitudinal cut through the tube 12 showing the canal 14 through which fluid flows.

The fluid will drain through canal 14 and will exit through the exit hole 15 and the superposed slit 16 into the inner cavity of the container 13, from where it will finally exit through holes 20 into the external space. As in the first mode of realization, the change in fluidic resistance is achieved by rotating plate 17 via the rotation imposed on the magnet 18 through the external magnetic field. Plate 17 is assembled so that is kept under some pressure against the base of the inner cavity of the container 13 (for example through a spring), leaving thus no space for the fluid to exit from the tube 12 other than through the slit 16. Hence, it is the relative position of the slit 16 with respect to hole 15 which determines what is the effective size of the exit hole, thus determining also the effective fluidic resistance of the system according to the principle of the invention. Preferably, the plate 17 has an axis (not shown) which penetrated into a hole of the container 13 to ensure proper relative rotation.

Figure 4:
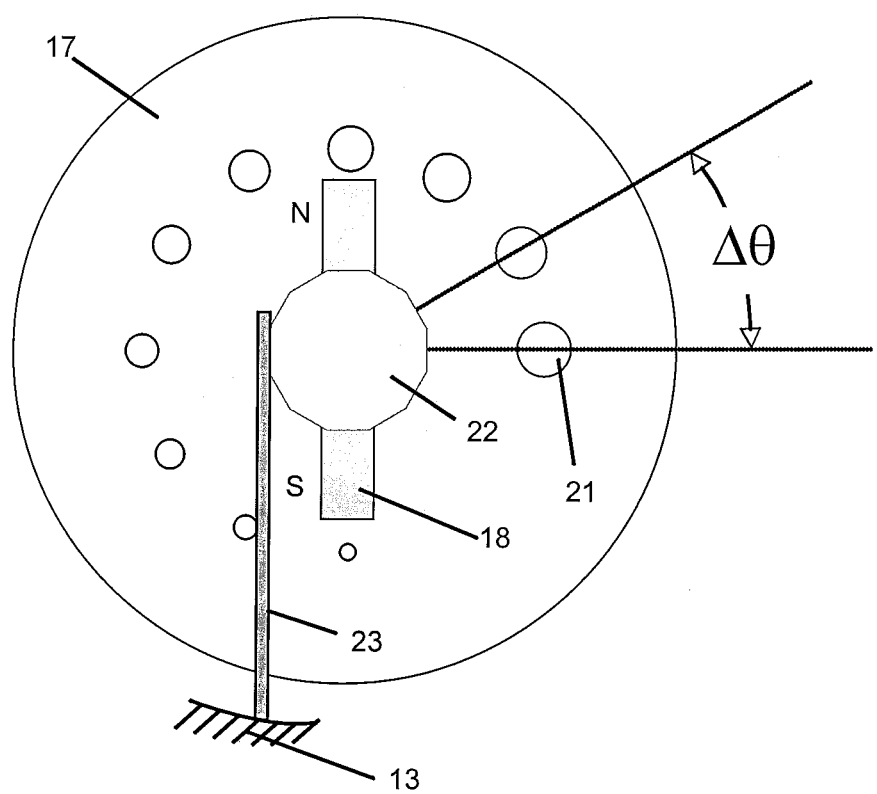
FIG. 4 illustrates a third embodiment of the invention.

In another design illustrated in FIG. 4, plate 17 may contain a plurality of holes 21 as opposed to the variable section slit 16. The holes have a progressively smaller diameter and are spaced on a circular arc with respect to the axis of rotation in a manner such that as the disk is rotated by a given angle $\Delta\theta$, one of the holes 21 will be on top and concentric with the exit hole 15. The angle of rotation between two successive holes $\Delta\theta$, is drawn here to be 30 degrees, but this can vary according to the number of holes and the desired resolution (fine regulation) in the change in fluidic resistance that one likes to achieve. To insure a rotation by increments of exactly the angle $\Delta\theta$, the plate 17 may comprise on its axis of rotation or in the periphery a "gear-like" system or equivalent system, which allows rotational steps of exactly the angle $\Delta\theta$. An example, among others, of such system is shown in FIG. 4. The dodecagonal "gear" 22 is concentric and attached to the plate 17. The stiff but flexible beam 23 is fixed to the wall of the container 13 and is pushing on one of the flat surfaces of dodecagonal "gear" 22 with a certain force F. Any rotation of the plate 17 less than $\Delta\theta$ will force the beam to be deflected to the left, increasing thus the contact force F. The contact force F will be restored into its minimum level when a rotation of exactly $\Delta\theta$ is achieved. Such a system guarantees two important functionalities:

1) It forces the system to take a position at the point of minimal energy, thereby guaranteeing that a rotation of exactly $\Delta\theta$ or multiples of that are performed.

2) It prevents accidental rotations of the plate due to external mechanical factors (i.e., physiological movements, shocks, variations in external magnetic fields, etc.).

It is clear that accidental or undesired rotation of the plate 17 due to variation of external magnetic fields (i.e., variations in the terrestrial magnetic field, etc.) may be prevented by correctly dimensioning the required applied magnetic field by means of the electromagnet 10, so that the latter is much greater than the naturally occurring external magnetic fields and sufficient enough to: a) overcome the frictional forces between the plate 17 and the bottom surface of container 13 and b) provide enough energy (moment) to flex the beam 23 and carry out the desired rotation.

It is evident that a similar system of successive holes can also replace the variable section slit 5 in FIG. 1. Further, a "gear" or other equivalent mechanical system similar the one explained earlier, which limits accidental rotations of the gasket 4, may also be included in the device shown in FIG. 1.

In another embodiment, the device according to the invention can include a miniaturized pressure sensor along the fluidic channel 14, preferably as close to the intraocular space as possible, connected to a miniaturized telemetry system which can be activated and energized from distance and which can send to an external receiver, telemetrically, the measured IOP signal. This feature will allow for an easy and non-invasive measurement of IOP.

The principle of the invention, i.e. sense the direction of magnetic fields within implanted devices and applying magnetic fields to move or rotate parts of said implanted devices can be of general utility for a variety of medical devices. One such example is the control of fluid flow within bodily conduits, such as vessels (veins or arteries) or other ducts (i.e., urinary duct, etc). An example of a further embodiment of the invention illustrating this principle is shown in FIG. 5.

In this design, the device containing an outer shell 24 connected through a hinge 26 to a clip 25 can be positioned around a vessel 27 so that the vessel is contained in the space between the clip 25 and a flexible and/or elastic membrane 28, which covers hermetically the device and prevents any contact of the internal mechanism of the device with the external fluids and tissues. The clip 25 is secured in place by a locking system 31. An elliptic-shaped cylinder 30 containing a magnet 29 can be rotated via applied external magnetic fields, as explained earlier, thereby pressing at variable degrees on the membrane 28, depending on its rotational position, and thus imposing variables degrees of constriction on the arterial cross sectional area. This, in turn, will lead to changes in hemodynamical resistance and control of flow. It is evident to any knowledgeable person in the field that the shape of the clip 25 and the rotating elliptic-shaped cylinder 30 can be chosen so as to optimize the effects of rotation on the shape of the contained vessel, to achieve optimal results (i.e., linear or prescribed change in cross-sectional area of the vessel per degree of rotation, etc.).

Figure 5:
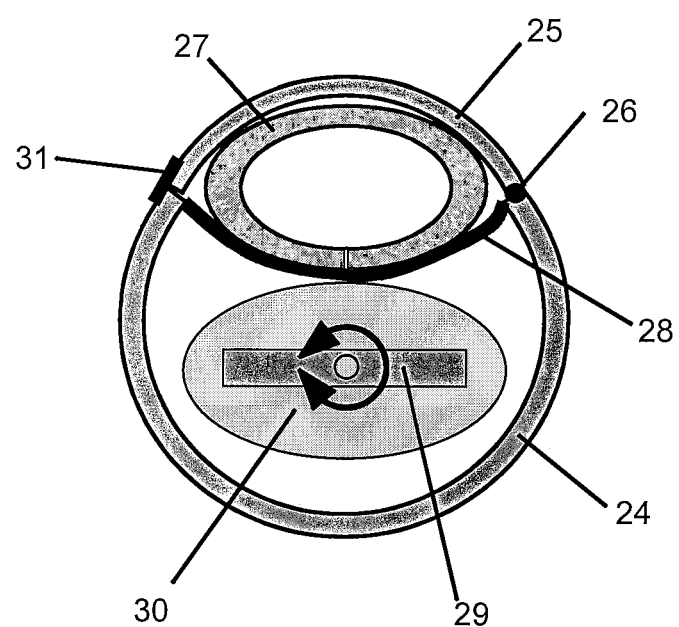
FIG. 5 illustrates a fourth embodiment of the invention.

In addition, this embodiment may be used in the device illustrated in FIG. 1 whereby the vessel 27 of FIG. 5 will be replaced by the inlet tube 1 to obtain the same regulation effect.

Also, it is possible to use a system equivalent to the gear 22 and beam 23 of FIG. 4 in order to carry out definite rotation of a given angle instead of continuous variations.

In a further embodiment, it is possible to apply the principle of the invention on the exit holes 6 (see FIG. 1) or 20 (see FIG. 3) and limit the flow leaving the chamber 2 or 13. Using the principle of the invention, the gasket could be designed to open one or more exit holes, depending on its angular position and thereby limit or increase the flow of liquid leaving the container. The same principle may be applied to the embodiment of FIG. 3 where one or more exit holes 20 may be opened to limit or increase the flow leaving the container 13.

In a further embodiment, instead of varying the section of the slit or the diameter of the holes, one could envisage to use a porous media with variable porosities. For example, all holes could have the same diameter and be covered with a sheath or other biocompatible fabric with different porosity. Another possibility, as illustrated in FIG. 6, is to have a continuous slit 16 of constant width, but have the slit covered with a sheath or fabric 32 or equivalent surface with a gradually changing porosity. For example, the change of porosity could be made by the addition of layers 32a, 32b, 32c, 32d, thus reducing the porosity when more layers are present.

In a variant, the slit or the holes could also change size even with such porous media added. This could allow a finer regulation of the flow.

Of course, the embodiments described above are non-limiting illustrative examples and variations using equivalent means are possible.

The invention claimed is:

1. An adjustable drainage implantable device comprising at least a tube for the passage of fluid to be drained, said tube passing through a first section of a chamber, said chamber comprising a second section separated from said first section by a membrane, rotating means for adjusting the flow rate in said tube by engaging the tube, said rotating means positioned in said second section, and said rotating means comprising a body that presses at variable degrees on the membrane depending on the rotational position of the rotating means and the membrane presses directly on the tube to impose continuously variable degrees of constriction on the tube sectional area.

2. The device as defined in claim 1, wherein said tube is adapted to connect to a vessel or a bodily duct.

3. The device as defined in claim 1, wherein said chamber is formed by said membrane and a clip.

* * * * *